United States Patent [19]

Choe et al.

[11] Patent Number: 4,701,187
[45] Date of Patent: Oct. 20, 1987

[54] PROCESS FOR SEPARATING COMPONENTS OF A GAS STREAM

[75] Inventors: Jung S. Choe, Allentown; Steven R. Auvil, Macungie; Rakesh Agrawal, Allentown, all of Pa.

[73] Assignee: Air Products and Chemicals, Inc., Allentown, Pa.

[21] Appl. No.: 926,695

[22] Filed: Nov. 3, 1986

[51] Int. Cl.$^4$ ............... B01D 53/22; B01D 53/04
[52] U.S. Cl. .................................. 55/16; 55/26; 55/58; 55/62; 55/68
[58] Field of Search .............. 55/16, 25, 26, 58, 62, 55/68, 66, 74, 75, 158

[56] References Cited

U.S. PATENT DOCUMENTS

| | | | |
|---|---|---|---|
| 4,130,403 | 12/1978 | Cooley et al. | 55/16 |
| 4,180,552 | 12/1979 | Graham et al. | 55/16 X |
| 4,229,188 | 10/1980 | Intille | 55/16 |
| 4,238,204 | 12/1980 | Perry | 55/16 |
| 4,255,591 | 3/1981 | Makin et al. | 55/16 X |
| 4,398,926 | 8/1983 | Doshi | 55/16 |
| 4,466,946 | 8/1984 | Goddin, Jr. et al. | 55/16 X |
| 4,518,399 | 5/1985 | Croskell et al. | 55/16 |
| 4,548,618 | 10/1985 | Linde et al. | 55/16 |
| 4,591,365 | 5/1986 | Burr | 55/16 |
| 4,602,477 | 7/1986 | Lucadamo | 55/158 X |
| 4,639,257 | 1/1987 | Duckett et al. | 55/16 |
| 4,645,516 | 2/1987 | Doshi | 55/16 |
| 4,654,063 | 3/1987 | Auvil et al. | 55/158 X |

Primary Examiner—Robert Spitzer
Attorney, Agent, or Firm—Mark L. Rodgers; William F. Marsh; James C. Simmons

[57] ABSTRACT

The present invention is a process for separating and recovering a component from a multi-component feed gas mixture. The feed gas mixture is initially separated in a membrane separation unit or units to produce a gas stream concentrated in the desired component. The concentrated gas stream is subsequently further separated in an adsorption unit having an adsorbent which selectively adsorbs non-desired gaseous components thereby producing a purified product stream. The non-desired gaseous components are subsequently desorbed and a purge stream from the adsorption unit containing the desorbed non-desired gaseous components along with a portion of the desired components is recycled to the feed gas mixture.

32 Claims, 2 Drawing Figures

PROCESS FOR SEPARATING COMPONENTS OF A GAS STREAM

TECHNICAL FIELD OF THE INVENTION

The present invention relates to the separation and recovery of a component from a multi-component gas stream.

BACKGROUND OF THE INVENTION

In the past, processes designed to produce a high purity product stream at high recovery from feed streams containing up to 90 mole % of the desired component required multiple stage membrane systems or multi-bed Pressure Swing Adsorption ("PSA") units. The use of stand-alone membrane units to produce a very high purity stream; i.e. greater than 99%, was found to be inefficient since large membrane areas and power demands were required in order to achieve this high purity at a high recovery. PSA units, on the other hand, provided to be very efficient in producing a high purity stream from feed streams containing the desired gas at concentrations greaters than 70 mole %, but become less efficient for treating relatively low purity; i.e. less than 70% streams to yield a high purity product at high recovery.

U.S. Pat. No. 4,229,188 teaches a process for recovering hydrogen from a gas mixture containing hydrogen and normally liquid hydrocarbons. The feed stream is passed to a selective adsorption unit to initially separate the feed, and the purge stream from the adsorption unit is subsequently treated in a membrane separator to recover an additional amount of the desired component. The process design disclosed in this patent, however, is only an efficient scheme for feed stream that are highly concentrated in the desired components; i.e. have a concentration of greater than 70 mole % of the desired component.

U.S. Pat. No. 4,238,204 discloses a process for recovering a light gas in both high purity and high yield from a gas mixture containing said light gas and other components. The gas mixture is initially directed to a selective adsorption unit which produces a high purity light gas and a purged gas containing at least a portion of the light gas. The purged gas from the adsorption unit is subsequently passed to a membrane permeator selectively permeable to the light gas in order to recover the permeated gas comprising light gas of improved purity from said permeator and recycling said permeated gas to the selective adsorption unit. As with U.S. Pat. No. 4,229,188, this process scheme is also only suitable for feed streams which are relatively highly concentrated in the desired feed component i.e. greater than 70 mole %.

U.S. Pat. No. 4,398,926 discloses a process for recovering hydrogen from a high pressure stream having a hydrogen content of up to about 90 mole %. The feed stream is passed to a separator containing a permeable membrane capable of selectively permeating hydrogen. The separator is used to achieve a bulk separation of the desired hydrogen component from impurities contained in the gas stream. The separated hydrogen is recovered at reduced pressure and passed to a pressure swing adsorption system adapted for operation at reduced pressure. Additionally, the off gas from the separator is recovered essentially at the higher pressure of the feed gas stream, and at least a portion of this stream is throttled to a lower pressure and passed to the pressure swing adsorption system as a co-feed gas in order to increase the recovery of the desired component.

BRIEF SUMMARY OF THE INVENTION

The present invention is a process for separating and recovering a desired component at high purity and high recovery from a multi-component gas stream comprising components which have different permeabilities through a semi-permeable membrane.

The process comprises passing the multi-component feed gas stream to a plurality of membrane separation units to produce a gas stream concentrated in one or more desired components. The concentrated stream is passed to an adsorption unit which contains an adsorbent which selectively adsorbs the non-desired gaseous components to produce a product stream which can have a concentration of up to 95 mole % or greater of the desired component. The gaseous components which are adsorbed in the adsorption unit are subsequently desorbed and recycled and combined with the feed gas stream entering the membrane separation unit. In some instances, a portion of the desorbed gas may be sufficiently concentrated in a particular component to be withdrawn as a purge or a co-product stream.

The present process provides an efficient means to recover one component from a gas mixture containing at least one other component. The interactions between the membrane and adsorption units compliment each other's operation to provide an efficient process for producing a high purity product stream at recoveries greater than can be achieved by either unit operated individually.

DETAILED DESCRIPTION OF THE INVENTION

Figure 1:
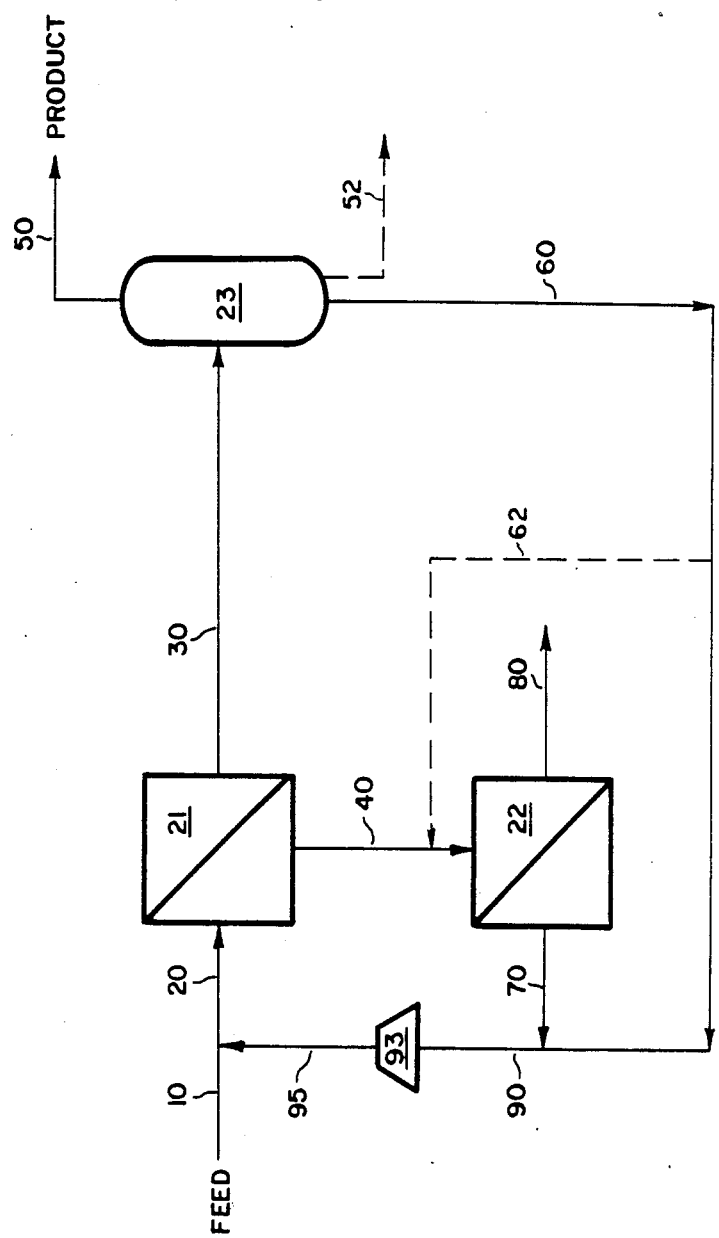
FIG. 1 is a schematic flow diagram of one embodiment of the present invention wherein the desired product is a more permeable component of the feed gas mixture.

The present invention is a process for recovering one or more components from a gas mixture. The process involves hybridizing a semi-permeable membrane-based unit or units with an adsorption unit. A multi-component feed gas mixture containing at least two major components wherein the permeation rate through a membrane unit of one major component is different from the other major components is passed to a plurality of membrane separation units to produce a gas stream concentrated in the desired component. A major component in a feed gas mixture is one whose concentration exceeds 1 volume %, and typically exceeds 4 volume %.

The membrane unit used in this invention can be any membrane device with some selectivity for separating one major gaseous component from the other major components in the feed gas mixture when a pressure differential is maintained across the membrane. Each membrane unit may consist of a single membrane device or, alternatively, several membrane devices plumbed and operated so as to achieve the separation in the most efficient manner; e.g., a cascade of membranes with internal recycle streams between various stages of the membrane unit. Typically, the membrane devices are manufactured in modules, each having certain semipermeable membrane areas for permeation. Semipermeable membrane materials currently available which can be employed in this process include: polysulfone, cellulose acetate, polyimide, polyamide, silicone rubber, polyphenylene oxide, etc.

The resultant stream from the membrane separation unit concentrated in one or more desired components; i.e., the concentrated stream, is passed to an adsorption unit which contains an adsorbent capable of selectively adsorbing non-desired components, thereby producing a product stream having a high concentration of the desired component. A product stream having a total concentration of the desired components up to at least 95 mole % and preferably greater than 99 mole % can be achieved. In typical embodiments, the product stream will represent at least an 80 mole % and preferably at least a 90 mole % recovery based upon the feed. The adsorption unit can be kinetic or equilibrium-based and operated as pressure swing, temperature swing, vacuum swing or any other suitable method or combination thereof. Examples of adsorbents typically used in these units include molecular sieves, such as carbon molecular sieves and zeolitic materials such as cation exchanged zeolites from the faujasite and mordenite families.

While the term adsorption is used herein, it should be realized that, depending upon the totality of operating conditions and gaseous components, absorption or other similar type purification units may suitably be substituted without deviating from the spirit of the invention.

The non-desired components which were adsorbed in the adsorption unit are subsequently desorbed and recycled along with a portion of the desired components to the feed gas mixture entering the membrane separation units. A portion of the desired components can be employed as a rinse stream for the adsorption unit following the desorption step. The rinse stream may then be recycled along with the desorbed components. At some point during the desorption cycle, the concentration of one or more of the non-desired components may be sufficiently high to purge a portion of this stream from the process or make it available as a co-product.

Units or systems to remove very low levels of contaminants such as $O_2$, $N_2$, $H_2$, $CO_2$, $H_2O$, etc. can be added to further treat any of the process streams. Such systems are commercially available and can be added as needed to any of the hybrid schemes of the present invention.

FIG. 1 represents one embodiment of the present invention wherein a more permeable component of the feed gas mixture is separated and recovered as a purified product. The gaseous feed mixture 10 containing, up to 90 mole % of the desired component, and preferably between 20-85 mole %, is mixed with the compressed recycle stream 95, to give a combined feed stream 20. The combined feed stream 20 is passed to a first membrane unit 21 to form a first permeate stream 30 and a first reject stream 40. The permeate stream 30, from the first membrane unit 21 is concentrated in the desired component and is fed to an adsorption unit 23 for a final purification to produce a purified product stream 50. Depending upon the pressure level of the permeate stream 30, the stream can optionally be compressed before it is fed to the adsorption unit 23. The first reject stream 40 from the first membrane unit, 21, is fed to a second membrane unit 22 to produce a second permeate stream 70 and a second reject stream 80. The recovery level of the desired component in the second permeate stream 70 from the second membrane unit 22 is fixed depending upon the desired recovery level or optimum recovery level determined by economic analyses. If necessary, one can fix the recovery level at this stage to be very high such that the overall product recovery level is greater than 99%; a level which is generally very difficult to achieve with the prior art schemes. The pressure of the second permeate stream 70 is generally fixed to be equivalent to that of the purge stream 60 from the adsorption unit 23 so that they can be mixed to form stream 90, compressed in compressor 93, and recycled as compressed stream 95 to the feed gas mixture 10. Alternatively, the streams could be at different pressures and fed to individual stages of compressor 93. The second reject stream 80 from the second membrane unit 22 may be recovered as a high pressure stream and either expanded separately to recover energy, or utilized for other operations or simply discarded. Depending upon concentration and composition, a portion of the desorbed components may optionally be recovered from the adsorption unit 23 as a co-product stream 52 and a separate portion 62 may optionally be passed through an intermediate membrane unit, such as unit 22, prior to being recycled. The key to this process scheme is to fix the recovery of the desired component at a moderate level (30–90%, particularly 50–80%) at the first membrane unit 21, and at a high level; i.e., >50% and preferably >80%, at the second membrane unit 22.

Particular gas mixtures which are well suited for separation via this process scheme include: hydrogen-carbon monoxide; hydrogen-hydrocarbon; helium-hydrocarbon; helium-hydrocarbon-nitrogen; and methane-nitrogen.

Figure 2:
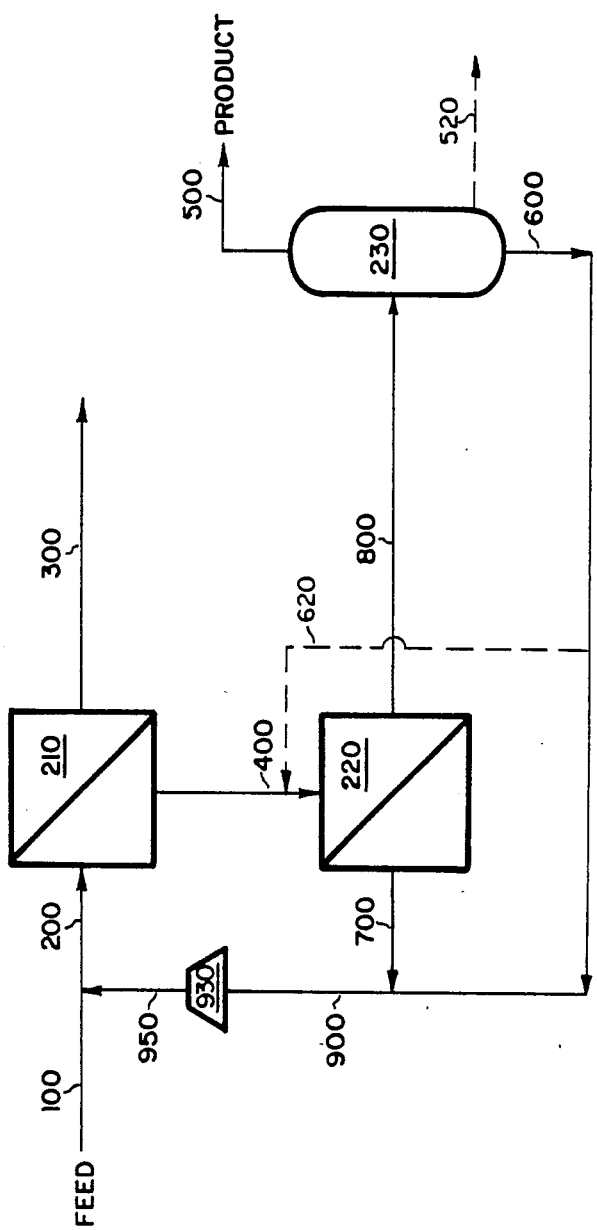
FIG. 2 is a schematic flow diagram of one embodiment of the present invention wherein the desired product is a less permeable component of the feed gas mixture.

FIG. 2 represents a process scheme that enriches one or more less permeable components as a reject stream in a series of membrane units and purifies the stream in an adsorption unit to recover the desired components as purified product. The major difference between this scheme from the one shown in FIG. 1 is that the adsorption unit 230, is used to purify the reject stream 800 from a second membrane unit 220.

The gaseous feed mixture 100, containing up to a total of 90 mole % and preferably between 20-85 mole % of the desired components is mixed with the compressed recycle stream 950 to produce a combined feed stream 200. The combined feed stream 200 is passed to a first membrane unit 210 to produce a first permeate stream 300 and a first reject stream 400. Depending upon the recovery level desired in the product stream 500, the first membrane unit 210 can be configured into a multistage membrane unit. The first permeate stream 300 is collected for subsequent use or simply discarded. The first reject stream 400 is passed to a second membrane unit 220 to produce a second permeate stream 700 and a second reject stream 800. The second reject stream 800, enriched in the desired components, is passed to an adsorption unit 230 containing an adsorption medium selective for adsorbing non-desired components, thereby producing a purified product stream 500, having a high concentration of the desired components.

The non-desired components are subsequently desorbed from the adsorption unit 230 as stream 600 and mixed with the second permeate stream 700 from membrane unit 200, which are generally at similar pressures, to form stream 900. Stream 900 is compressed to about feed pressure in compressor 930 to form compressed stream 950 which is subsequently combined with the feed gas mixture 100. Alternatively, streams 600 and 700 may be at different pressures and can be fed to individual stages of the compressor 930. Depending upon concentration and composition, a portion of the desorbed components may optionally be recovered from the adsorption unit 230 as a co-product stream 520 and a separate portion 620 may optionally be passed through an intermediate membrane unit, such as unit 220, prior to being recycled. Gas mixtures which are well suited for separation using this process scheme include: argon-oxygen; inert gas (nitrogen and argon)-oxygen, hydrocarbon-carbon dioxide; argon-NH$_3$ purge gas; and nitrogen-methane.

In all of the process schemes of the present invention, optional compressors or expanders may be utilized to vary the pressure of any of the gas streams, depending upon the gas mixture, treatment and product pressure, and pressure difference between any two streams which are subsequently combined. Compressors 93 and 930 in FIGS. 1 and 2 respectively are only representative of particular embodiments and may be repositioned or eliminated as other process conditions are altered.

The examples presented below are presented only to illustrate the invention and are not meant to limit the scope of the invention.

EXAMPLE 1

The objective of this example is to produce a purified helium (99.9+ mole %) stream at 210 psia from a 665 psia gas mixture containing 58.2 mole % helium. The properties of the feed gas stream are set out in Table 1 below.

TABLE 1

| Feed Rate | = 240 lb. moles/hr. |
|---|---|
| Pressure | = 665 psia |
| Temperature | = 110° F. |
| FEED GAS COMPOSITION: | |
| Component | Mole Percent |
| Helium | 58.2 |
| Nitrogen | 40.5 |
| Methane | 1.3 |

Process calculations were done for a membrane/PSA process in accordance with the present invention as depicted in FIG. 1 (case 1) and also for several prior art membrane/PSA process (cases 2 to 3).

Case 1

The feed stream 10, is first mixed with the recycle stream 95 to form a mixed stream 20 having a helium concentration of 66.6 mole %. Mixed stream 20 is then fed to the first membrane unit 21 to form a first permeate stream 30 and a first reject stream 40. The permeate stream 30, containing 95% helium, is recovered at 220 psia and is fed to a PSA unit 23 to recover a purified helium product stream 50 at greater than 99 mole % purity at 99.4 mole % recovery. The purified helium product stream 50 is then either sold as a gaseous product or sent to a liquefying process. The reject stream 40 from the first membrane unit 21 is at almost the same pressure as the fresh feed 10 and is fed to the second membrane unit 22 to recover an additional amount of helium. The helium recovery level at the second membrane unit 22 is fixed depending upon the overall desired helium recovery. The pressure of the permeate stream 70 from this membrane stage is the same as the purge stream 60 containing non-desired components, i.e. nitrogen and methane, desorbed from the PSA unit. Streams 60 and 70 are combined and compressed in compressor 93 to the pressure of the feed 10 and recycled to form a combined feed stream 20. The reject stream 80 from the second membrane unit 22 which consists mainly of nitrogen and methane components can be directly expanded to recover its energy or can be sent to a helium liquefaction areas to provide makeup nitrogen and/or to recover its energy.

The details of the key process streams for this process are given in Table 2 below.

A summary of the total helium recovered, relative power consumed, and relative membrane area required for this case is presented in Table 3 below. Although the helium recovery is very high, modifications of the operating conditions of the membrane and PSA units can further increase recovery.

TABLE 2

| Key Process Streams for the Membrane/PSA Hybrid Process of FIG. 1, Example 1, Case 1 | | | | | | | | |
|---|---|---|---|---|---|---|---|---|
| Stream Number | 10 | 100 | 20 | 30 | 40 | 80 | 70 | 50 |
| Pressure (psia) | 665 | 665 | 665 | 220 | 660 | 655 | 25 | 210 |
| Total Flow (lb. moles/hr) | 240 | 127.4 | 367.4 | 208.6 | 158.8 | 101.3 | 57.5 | 138.8 |
| Composition (mole %) | | | | | | | | |
| Helium | 58.2 | 82.3 | 66.6 | 95.0 | 29.2 | 0.9 | 79.0 | 100.0 |
| Nitrogen | 40.5 | 17.1 | 32.4 | 4.8 | 68.6 | 96.0 | 20.4 | — |
| Methane | 1.3 | 0.6 | 1.0 | 0.2 | 2.2 | 3.1 | 0.6 | — |

Case 2

In this case a membrane unit is primarily used as a preprocessor to upgrade the feed stream to a desired level of helium purity before the stream is fed to the adsorption unit. The feed gas mixture set out in Table 1 was first treated in a membrane unit to give a permeate stream containing 95% helium at 220 psia as was done in Case 1. This helium-enriched stream is then sent to the PSA unit to produce a purified helium stream at a 210 psia pressure. Although this scheme uses less membrane area and power, it suffers from a significantly lower helium recovery as depicted as case 2 in Table 3 below.

Case 3

The feed gas mixture of Table 1 was treated in a scheme wherein a first membrane unit is used to recover the desired level of helium from the feed stream and a second membrane unit is used to produce a helium stream sufficiently enriched so that it can be fed to a PSA unit.

The feed stream is first mixed with the helium enriched stream from the second membrane unit. This mixed stream is then fed to the first membrane unit. The helium recovery level at this stage is fixed such that the overall helium recovery level is consistent with Case 1. The permeate stream from the first membrane unit is then mixed with the purge stream from the PSA unit, compressed and subsequently fed to the second membrane unit. The permeate stream from the second membrane unit is recovered at a 220 psia pressure and fed to the PSA unit to produce a helium product stream.

In general, this scheme differs from the new concept in that the first membrane unit, which processes a large stream, is required to operate at a very high recovery level. As shown in Table 3, this scheme (case 3) uses more power and membrane area than the new suggested concept.

TABLE 3

Comparison of the Cases Presented in Example 1

| | Case 1 | Case 2 | Case 3 |
|---|---|---|---|
| Helium Recovery (%) | 99.4 | 43.5 | 99.4 |
| Relative Power | 1.0 | 0.0 | 1.76 |
| Relative Area | 1.0 | 0.26 | 1.10 |

In summary, Example 1 clearly illustrates that the process scheme of the present invention (case 1) gives a purified product stream at very high recovery and is also very efficient compared to other schemes previously used to separate gas mixtures.

EXAMPLE 2

The following example illustrates the embodiment shown in FIG. 2. This concept is an attractive process scheme when the desired product is a less permeable component through the membrane units, which can be purified and recovered as a raffinate stream from the adsorption unit. This embodiment has an added advantage in that the desired product can be recovered as a high pressure stream without additional compression.

Calculations were done to produce a high purity argon stream from a gas mixture containing 50% oxygen and 50% argon. The membrane characteristics used to simulate this example are for advanced membranes currenty being developed; for example, U.S. Pat. No. 4,584,359 teaches a cobalt complex vinyl polymer membrane that possesses a very high permeability of oxygen with respect to other components such as nitrogen, argon, etc. The PSA unit used to simulate this case is a kinetic-based system which preferably adsorbs oxygen over argon; however, this particular PSA unit can be replaced with an equilibrium-based unit depending upon the specific separation desired in a process situation.

In this process, the feed stream, 100, is first mixed with the recycle stream, 950, before it is fed to the first membrane unit, 210 as stream 200 having a 52.1 mole% argon concentration, The permeate stream 300 from the first membrane unit 210 contains about 97% oxygen and is recovered at a 20 psia pressure. Again, the oxygen recovery at the feed stage membrane unit is fixed at a relatively low level (~50%) in order to increase the oxygen purity and to minimize the argon losses in the permeate stream 300. The reject stream 400 has a concentration of 68.2 mole % argon and is directly fed to the second membrane unit 220 to produce an argon-enriched reject stream 800, having an argon concentration of 97.5 mole %, at a high pressure and to recover an argon-lean permeate stream 700 which is recycled after recompression. The oxygen recovery level at the second membrane unit can vary depending upon the argon purity and recovery desired for the second reject stream 800. The argon-enriched second reject stream 800 is then fed to the PSA unit to produce a purified argon product stream 500 at a concentration near 100% at high pressure. The purge stream 600 from the PSA unit is at 20 psia pressure and is mixed with permeate stream 700 from the second membrane unit and recycled to the feed.

The details of the feed stream and the other key process streams for this process scheme are given in Table 4 below. These calculations were done based on the assumptions that all permeate streams from the membrane units and the purge stream from the PSA unit were maintained at 20 psia pressure, and the argon recovery at the PSA unit was fixed at 50%.

TABLE 4

Key Process Streams for the Membrane/PSA Hybrid Process of Example 2

| Stream Number | 100 | 950 | 200 | 300 | 400 | 800 | 700 | 500 |
|---|---|---|---|---|---|---|---|---|
| Pressure (psia) | 410 | 410 | 410 | 20 | 405 | 400 | 20 | 380 |
| Total Flow (lb. moles/hr) | 100 | 109.1 | 209.1 | 51.7 | 157.4 | 99.2 | 58.2 | 48.3 |
| Composition (mole %) | | | | | | | | |
| Oxygen | 50 | 45.9 | 47.9 | 96.7 | 31.8 | 2.5 | 81.7 | — |
| Argon | 50 | 54.1 | 52.1 | 3.3 | 68.2 | 97.5 | 18.3 | 100.0 |

The data reported in Table 4 above show that the process scheme carried out in Example 2 above provides for the recovery of an argon product stream having a purity of about 100%. Total argon recovery is also very high since the only argon lost from the system is that contained in the permeate from the first membrane unit which is regulated to keep the argon loss at a minimum.

EXAMPLE 3

A second particular process scheme was carried in accordance with the general scheme illustrated in FIG. 2. In this scheme, the permeate stream 300 from the first membrane unit 210 is further processed in a separate membrane unit (not shown) to increase the purity of the more permeable component thus increasing the recovery of the desired less permeable component.

Calculations were done to produce a high purity methane stream 500 from a gas mixture containing 55% methane, 41% carbon dioxide, and a remaining mixture containing nitrogen, oxygen and water vapor. This gas composition is typical of landfill gas. Characteristics of currently available membranes were used to simulate this process and the adsorption unit used was a PSA unit such as kinetic-based or equilibrium-based system which preferably adsorbs carbon dioxide over methane.

In this process, the feed stream 100 is first mixed with the purged stream from the PSA unit and the mixed stream is compressed to an intermediate pressure of about 100 psia. After compression, this mixed stream is then mixed with the permeate stream from the second membrane separation unit 220. The resultant stream is then compressed to a feed pressure of about 775 psia and is passed to the first membrane unit 210 as feed stream 200. The permeate steam 300 from the first membrane unit 210 contains about 93% carbon dioxide and is at about 105 psia pressure. The carbon dioxide recovery at the feed stage membrane unit is fixed at a relatively low level (50%) to increase the carbon dioxide purity; however, this stream still contains about 6% methane, which represents about 10% methane lost to the overall process if not recovered. The permeate stream 300 is, therefore, sent to an additional membrane unit (not shown) where further purification of carbon dioxide or further recovery of methane is accomplished. The resultant purified stream from this additional membrane unit contains 98.5% carbon dioxide and only 0.7% methane. The reject stream produced from this additional membrane unit contains 89% carbon dioxide and 10% methane, and is recycled at about 100 psia pressure to the feed gas entering the first membrane unit 210.

The reject stream 400 from the first membrane unit 210 has a methane concentration of 51% and is directly fed to the second membrane unit 220 to produce a methane-enriched reject stream 800 having a methane concentration of 80%, at a high pressure and a methane-lean permeate stream 700 at about 100 psia pressure. The methane-enriched reject stream 800 from the second membrane unit 220 is subsequently fed to PSA unit 230 to produce a purified methane product stream 500 at a concentration of about 98% or higher at high pressure.

The gas adsorbed in the PSA unit 230; i.e., carbon dioxide, can be recovered as a purified carbon dioxide co-product stream or alternatively, the total desorbed gas mixture 600 can be recycled and mixed with the feed stream 100.

The details of the feed stream and the other key process streams for this example are given in Table 5 below. These calculations were based on a 70% methane recovery at the PSA unit.

400 from the membrane unit 210 forms the feed to a second membrane unit 220 and is separated to provide reject stream 800 containing 5% $H_2$ and 24.9% argon. The concentration of hydrogen in this stream determines the relative amount of argon and hydrogen in the product stream 500 from the adsorption unit 230. A smaller concentration of hydrogen will give stream 500 a higher argon concentration thus reducing further purification requirements but the membrane area of unit 220 must be enlarged and the permeate stream from membrane unit 220 would increase for recycle. For any given application, a detailed economic analysis would dictate the optimum combination of hydrogen and argon in stream 800 which is passed to the adsorption unit 230. In the present analysis, it was arbitrarily chosen to be 5% $H_2$. The permeate stream 700 from membrane unit 220 containing 3.9% argon is recycled to the first membrane unit 210. The presence of this recycle back to the feed stream allows the present process to be run with a high recovery of argon.

The reject stream 800 from the second membrane unit 220 contains 24.9% argon and is sent to a adsorption unit capable of adsorbing nitrogen and methane relative to argon and hydrogen. The recovery of $N_2$ and $CH_4$ from the adsorption process was taken to be 90% and that of argon to be 50%. Consequently the adsorption process not only produces a product stream 500 containing 83.3% argon and 16.7% $H_2$ but also produces a co-product stream 520 containing 63.9% $N_2$ and 35.1% $CH_4$. A purged stream 600 is also recovered from the adsorption unit to form a part of the recycled stream 950 to the first membrane unit 210. This recycled stream keeps the total argon recovery for the overall process at a high level; i.e., about 86%.

TABLE 5

| Key Process Streams for the Membrane/PSA Hybrid Process of Example 3 | | | | | | | | | |
| --- | --- | --- | --- | --- | --- | --- | --- | --- | --- |
| Stream Number | 100 | 900 | 600 | 200 | 300 | 400 | 700 | 800 | 500 |
| Pressure (psia) | 15 | 100 | 20 | 775 | 105 | 770 | 100 | 765 | 750 |
| Total Flow (lb. moles/hr) | 226 | 308 | 94 | 620 | 211 | 409 | 188 | 221 | 127 |
| Composition (mole %) | | | | | | | | | |
| Methane | 54.6 | 23.8 | 55.3 | 35.7 | 6.2 | 50.8 | 16.8 | 80.0 | 98.2 |
| Carbon Dioxide | 41.2 | 74.8 | 41.5 | 62.9 | 93.1 | 47.5 | 82.3 | 17.7 | 0.8 |
| Nitrogen | 1.0 | 0.4 | 1.0 | 0.6 | 0.1 | 0.9 | 0.2 | 1.4 | 1.0 |
| Oxygen | 0.2 | 1.0 | 2.2 | 0.7 | 0.3 | 0.8 | 0.7 | 0.9 | — |
| Water | 3.0 | 0.0 | 0.0 | 0.1 | 0.3 | 0.0 | 0.0 | 0.0 | — |

The data reported in Table 5 above shows that the process being carried out in Example 3 provides for the recovery of a methane product stream having a purity of about 98% and a recovery greater than 99%.

EXAMPLE 4

A process was simulated for the recovery of argon from ammonia purged gas in accordance with the general scheme set out in FIG. 2. The ammonia purge gas which forms the feed stream 100 has a composition of about 62% hydrogen, 20% nitrogen, 11% methane and 7% argon is under a pressure of approximately 2,000 psia and at a temperature of about 95° F. This stream is obtained from an ammonia plant after the removal of ammonia from the purged gas by any known technique, such as by absorption.

The feed stream 100 is combined with recycled stream 950 to give a combined feed 200 containing 70% $H_2$ and 8.7% Ar and is fed to a first membrane unit 210. The permeate stream 300 from the first membrane unit 210 contains 97.5% hydrogen and sent back to the ammonia plant. The recovery of hydrogen from this process is high; i.e., about 98%. The non-permeate stream The argon product, stream 500, contains some hydrogen which can be removed by any known process or combination of processes, for example argon could be cryogenically condensed or hydrogen could be removed by oxidation after which the water formed could be condensed and/or adsorbed, or an additional membrane unit could be used to remove the hydrogen.

Conventionally, argon is recovered from ammonia purged gas by cryogenic means. Such cryogenic systems are complicated and costly, requiring an attendant refrigeration system for the operation of a low-temperature separation unit. Moreover, the cryogenic plants are not amenable to quick turn downs and encounter problems associated with feed gas variations and plant stability. This is due to the fact that the cryogenic units are subject to operational variances of the ammonia plant and not vice versa. See, Isalski, W. H., "25 Years of Purged Gas Recovery" Nitrogen, 101, 152 (1984). The present process scheme which consists of a membrane unit followed by an adsorption unit is more amenable to feed turn downs and is easier to operate than previous methods.

The details of the key process streams obtained from the simulation of the above-described process are set out in Table 6 below.

TABLE 6

| Key Process Streams for the Membrane/PSA Hybrid to Recover Argon from NH₃ Purge Gas, Example 4 | | | | | | | | |
|---|---|---|---|---|---|---|---|---|
| Stream Number | 100 | 950 | 200 | 300 | 800 | 700 | 500 | 520 |
| Pressure (psia) | 2,000 | 2,000 | 2,000 | 350 | 1,980 | 15.0 | 600 | 15.0 |
| Total Flow (lb. moles/hr) | 100.0 | 73.6 | 173.6 | 62.3 | 47.9 | 63.4 | 7.2 | 30.5 |
| Composition (mole %) | | | | | | | | |
| $H_2$ | 62.0 | 80.8 | 70.0 | 97.5 | 5.0 | 92.0 | 16.7 | 0.2 |
| $N_2$ | 20.0 | 5.2 | 13.7 | 0.8 | 45.2 | 2.6 | — | 63.9 |
| $CH_4$ | 11.0 | 2.9 | 7.6 | 0.4 | 24.9 | 1.5 | — | 35.1 |
| Ar | 7.0 | 11.1 | 8.7 | 1.2 | 24.9 | 3.9 | 83.3 | 0.8 |

As can be seen from the results reported in Table 6 above, a product stream rich in argon can be obtained from the present process. While the product stream consists of two different components, in general this is not a problem because the two resultant components may be easily separated or used together, with the real problem of removing nitrogen and methane, being solved by the process.

EXAMPLE 5

The process scheme as depicted in FIG. 2 was simulated for the separation and recovery of 99.5% inert gas (nitrogen and argon) from air. This scheme is almost identical to the case presented in Example 2 above, with the difference being that the feed gas mixture is air, and the major component besides oxygen is nitrogen instead of argon. The present scheme was developed for air separation using membrane characteristics representing currently available membranes, and a kinetic-based PSA system.

One particular benefit of this process scheme is that the PSA unit is used to adsorb ~2-10% oxygen versus ~21% oxygen in a stand-alone unit, thereby increasing the inert gas recovery and productivity of the PSA unit. Another benefit of this process scheme is that most of the contaminants; e.g., CO₂, H₂O, etc., contained in the air will be removed by the membrane units. This improves the operation of the adsorption unit since typical adsorbents prefer CO₂ and H₂O over O₂.

Since the primary value associated with the feed gas for this application is the power used to compress it, additional flexibility is added to the cycle so that, if the oxygen purity of the second permeate stream 700 from membrane unit 220 is greater than that of air, it may be mixed with the first permeate stream 300 and recovered as an oxygen-enriched stream instead of being combined with the desorbed stream 600 and recycled to the feed gas. This can be done for this particular application because product recovery is less of a concern with the inert gas product (stream 500) purity being the most important parameter.

The details of the key process streams for this example are given in Table 7 below. These results clearly indicate that the process scheme depicted in FIG. 2 is suitable for recovering an inert gas (i.e., nitrogen and argon) at high purity, i.e. 99.5 mole % from an air feed. The first permeate stream 300 from the first membrane unit 210 can also be recovered as an oxygen-enriched stream; i.e., 39 mole % oxygen.

It was calculated that this process scheme can recover as much as twice the amount of product at less power consumption than either the kinetic-based adsorption unit or membrane unit when used as a stand-alone process.

TABLE 7

| N₂ Recovery from Air Via Membrane/Adsorption Hybrid Key Process Streams for the Membrane/PSA Hybrid Process of Example 5 | | | | | | | |
|---|---|---|---|---|---|---|---|
| Stream Number | 100 | 950 | 200 | 300 | 400 | 800 | 500 |
| Pressure (psia) | 15 | 15 | 175 | 15 | 170 | 120 | 100 |
| Total Flow (lb. moles/hr) | 64 | 51 | 115 | 33 | 81 | 81 | 30 |
| Composition (mole %) | | | | | | | |
| Oxygen | 20.36 | 15.5 | 18.4 | 38.9 | 10.0 | 10.0 | 0.5 |
| Nitrogen | 75.90 | 83.9 | 80.3 | 58.1 | 89.4 | 89.4 | 98.8 |
| Argon | 0.91 | 0.6 | 0.8 | 1.1 | 0.6 | 0.6 | 0.7 |
| Carbon Dioxide | 0.03 | — | — | 0.1 | — | — | — |
| Water | 2.80 | — | 0.5 | 1.8 | — | — | — |

In gas separation processes, when the product gas has a high value, a very high purity and recovery are often desired. The present invention provides process schemes that can efficiently recover a purified product (99+%) at high recovery (80+%) from a gas mixture containing at least one other component. The method of the present invention takes advantage of the favorable characteristics and minimizes the deficiencies of the membrane and adsorption units.

Stand-alone membrane units are generally considered very efficient for bulk separations on a relatively smaller scale, however, these systems are not generally efficient, if not impractical, in producing a high purity product (>99%) at very high recovery (>90%). When membrane units are used in a cascade to get high recoveries and/or purities, intermediate compression is often required and a relatively large amount of energy and membrane area are necessary.

Stand-alone adsorption units, on the other hand, are very effective in producing a purified gas stream, but they require the purity of feed streams to be relatively high; e.g., 70%. The performance of these units generally suffers from a relatively low recovery which can be further reduced if the pressure of the feed is very high.

The present invention not only gives a purified product stream at high recovery but also consumes much less power and/or results in substantial process simplifications, reduced investments, and improved economics. Many embodiments of the invention provide for the recovery of a second product stream enriched in a component other than that of the purified product.

Having thus described the present invention, what is now deemed appropriate for Letters Patent is set out in the following appended claims.

What is claimed is:

1. A process for recovering a desire component from a multi-component feed gas stream, said process comprising:
   (a) passing said feed gas stream to a plurality of membrane separation units to produce a stream concentrated in the desired component;
   (b) passing said concentrated stream to an adsorption unit containing an adsorbent that selectively adsorbs non-desired gaseous components present in said stream to produce a product stream further concentrated in the desired component;
   (c) desorbing the gaseous components from said adsorbent; and
   (d) recycling said desorbed gaseous components to the feed gas stream entering the membrane separation units.

2. A process in accordance with claim 1 wherein at least a portion of the desorbed gaseous components is recovered as a co-product.

3. A process in accordance with claim 1 wherein a stream depleted in the desired component is also produced by the plurality of membrane separation units.

4. A process in accordance with claim 1 wherein at least a portion of said desorbed gaseous components are passed through an intermediate membrane unit prior to being recycled to the feed gas.

5. A process in accordance with claim 1 wherein said adsorption unit is operated as pressure swing, vacuum swing, temperature swing or a combination thereof.

6. A process in accordance with claim 1 wherein said adsorption unit is rinsed with a portion of the desired component after the adsorbed components are desorbed.

7. A process in accordance with claim 6 wherein said portion of the desired components used to rinse the adsorption unit are recycled along with the desorbed components to the feed stream.

8. A process for separating a more permeable component of a multi-component feed gas mixture from a less permeable component and subsequently recovering said more permeable component as a purified product, said process comprising:
   (a) passing said multi-component feed gas mixture to a first membrane separation unit to produce a first permeate stream and a first reject stream;
   (b) passing said first permeate stream to an adsorption unit containing an adsorbent which selectively adsorbs less permeable components present in said permeate stream thereby producing a purified product stream;
   (c) desorbing the less permeable components from said adsorbent;
   (d) recycling said desorbed components to the feed gas stream entering the first membrane separation unit;
   (e) passing said first reject stream to a second membrane-separation unit to produce a second permeate stream and a second reject stream; and
   (f) combining said second permeate with said desorbed components prior to being recycled to the feed gas stream.

9. A process in accordance with claim 8 wherein at least a portion of said desorbed components is recovered as a co-product.

10. A process in accordance with claim 8 wherein at least a portion of said desorbed gaseous components are passed through the second membrane-separation unit prior to being recycled to the feed gas.

11. A process in accordance with claim 8 wherein said multi-component feed gas mixture contains helium as a more permeable component and nitrogen or hydrocarbons as a less permeable component.

12. A process in accordance with claim 8 wherein said multi-component feed gas mixture contains hydrogen as a more permeable component and carbon monoxide or hydrocarbons as a less permeable component.

13. A process in accordance with claim 8 wherein said adsorption unit is operated as pressure swing, vacuum swing, temperature swing or a combination thereof.

14. A process in accordance with claim 8 wherein the second reject stream is collected as a second product.

15. A process in accordance with claim 8 wherein said feed gas mixture has a concentration of between 20–85 mole % of the more permeable component.

16. A process in accordance with claim 8 wherein the combined desorbed components and the second permeate stream are compressed to feed gas pressure prior to being combined with the feed gas stream.

17. A process in accordance with claim 8 wherein the purified product stream has a concentration of greater than 99 mole % of the more permeable component.

18. A process for separating a less permeable component of a multi-component feed gas mixture from a more permeable component and subsequently recovering said less permeable component as a purified product, said process comprising:
   (a) passing said multi-component feed gas mixture to a first membrane separation unit to produce a first permeate stream and a first reject stream;
   (b) passing said first reject stream to a second membrane separation unit to produce a second permeate stream and a second reject stream;
   (c) passing said second reject stream to an adsorption unit containing an adsorbent which selectively adsorbs more permeable components present in said reject stream thereby producing a purified product stream;
   (d) desorbing the more permeable components from said adsorbent; and
   (e) recycling said desorbed components to the feed gas stream entering the first membrane separation unit.

19. A process in accordance with claim 18 wherein at least a portion of the desorbed components is recovered as a co-product.

20. A process in accordance with claim 18 wherein at least a portion of said desorbed gaseous components are passed through the second membrane-separation unit prior to being recycled to the feed gas.

21. A process in accordance with claim 18 wherein said purified product stream has a concentration greater than 99 mole % of the less permeable component.

22. A process in accordance with claim 18 wherein said second permeate stream is combined with the desorbed components from the adsorption unit prior to being recycled to the feed gas stream.

23. A process in accordance with claim 18 wherein said first permeate stream is collected as a second product stream enriched in a component other than that of the purified product stream.

24. A process in accordance with claim 23 wherein said second permeate stream is combined with the first permeate stream and collected as a combined permeate stream.

25. A process in accordance with claim 18 wherein the feed gas mixture comprises argon as a less permeable component and oxygen as a more permeable component.

26. A process in accordance with claim 18 wherein the purified product stream comprises one or more hydrocarbons.

27. A process in accordance with claim 18 wherein said adsorption unit is operated as pressure swing, vacuum swing, temperature swing or a combination thereof.

28. A process for separating nitrogen from air and subsequently recovering nitrogen as a purified product, said process comprising:
(a) passing an air stream to a membrane separation unit to produce an oxygen-enriched permeate stream and a reject stream;
(b) passing said reject stream to an adsorption unit containing an adsorbent which is selective for oxygen, thereby producing a purified nitrogen product stream; and
(c) desorbing the oxygen from the adsorbent and recycling it back to the air stream entering the separator.

29. A process in accordance with claim 28 wherein said reject stream is further separated by a second membrane prior to being passed to the adsorption unit, thereby producing a second oxygen-enriched stream and a reject stream which is then passed to the adsorption unit.

30. A process an accordance with claim 29 wherein both oxygen-enriched permeate streams are combined and collected as a second product.

31. A process in accordance with claim 28 wherein the adsorption unit is rinsed with a portion of the nitrogen product after the oxygen is desorbed.

32. A process in accordance with claim 28 wherein said purified nitrogen is recovered along with argon as a purified inert product stream.

* * * * *